(12) United States Patent
Lan-Hargest et al.

(10) Patent No.: US 6,693,132 B2
(45) Date of Patent: Feb. 17, 2004

(54) METHODS FOR USING ALKANOYLOXYMETHYL ESTERS

(75) Inventors: Hsuan-Yin Lan-Hargest, Fallston, MD (US); Norbert L. Wiech, Phoenix, MD (US)

(73) Assignee: Beacon Laboratories, Inc., Phoenix, MD (US)

( * ) Notice: Subject to any disclaimer, the term of this patent is extended or adjusted under 35 U.S.C. 154(b) by 0 days.

(21) Appl. No.: 09/742,729

(22) Filed: Dec. 21, 2000

(65) Prior Publication Data

US 2002/0143055 A1 Oct. 3, 2002

(51) Int. Cl.$^7$ ............................................. A61K 31/225
(52) U.S. Cl. ........................................................ 514/547
(58) Field of Search ......................................... 514/547

(56) References Cited

U.S. PATENT DOCUMENTS

| | | |
|---|---|---|
| 3,931,412 A | 1/1976 | Kensler, Jr. et al. ........ 424/313 |
| 4,012,526 A | 3/1977 | Kensler, Jr. et al. ........ 424/313 |
| 5,569,675 A | 10/1996 | Rephaeli et al. ............. 514/547 |
| 5,939,455 A * | 8/1999 | Rephaeli ....................... 514/547 |
| 5,962,523 A * | 10/1999 | Moran et al. ................. 514/547 |
| 6,110,955 A | 8/2000 | Nudelman et al. .......... 514/411 |
| 6,110,970 A | 8/2000 | Nudelman et al. .......... 514/537 |

FOREIGN PATENT DOCUMENTS

| | | |
|---|---|---|
| EP | 0 302 349 | 2/1989 |
| WO | WO 98/17273 | 4/1998 |

OTHER PUBLICATIONS

Nudelman, A, et al., "Novel Anticancer Prodrugs of Butyric Acid", Journal of Medicinal Chemistry, vol. 35, No. 4, pp. 687–694, (1992).

* cited by examiner

Primary Examiner—Phyllis G. Spivack
(74) Attorney, Agent, or Firm—Fish & Richardson P.C.

(57) ABSTRACT

Methods of using propionoyloxymethyl propionate ("POMP") and butyroyloxymethyl butyrate ("BOMB") are disclosed. Methods of treating cancer using these compounds are disclosed. The compounds are effective in the inhibition of histone deacetylase.

21 Claims, 2 Drawing Sheets

METHODS FOR USING ALKANOYLOXYMETHYL ESTERS

FIELD OF THE INVENTION

The present invention relates to methods of using propionoyloxymethyl propionate and butyroyloxymethyl butyrate in the treatment of cancer and other proliferative diseases, hemoglobinopathies and inherited metabolic disorders and to treat or alleviate various other disorders and to treat or alleviate various other illnesses and conditions, such as by hematopoietic stimulation. The present invention also relates to methods for using the disclosed compounds in the inhibition of histone deacetylase.

BACKGROUND INFORMATION

Histones are unique proteins in the nucleus of a cell. DNA is wound around a complex of histones to form nucleosomes. As such, histones are an integral structural element of the chromatin material. The histones complexed with the DNA are susceptible to a range of chemical modifications, one of which is acetylation, and the reverse of which is deacetylation. Acetylation of histone protein is believed to facilitate transcription of the DNA, thereby enhancing gene expression. Histone deacetylase is believed to reverse the process that represses gene expression. Histone dynamics are regulated by two enzymes—histone acetyl transferase and histone deacetylase.

Hyperacetylation due to inhibition of histone deacetylation, and the resulting expression of a latent gene, have been observed or proposed to occur in numerous inherited metabolic diseases and in cancer. The inhibition of histone deacetylase is believed to activate an otherwise dormant fetal gene, which serves as a redundant or back-up gene. Pharmacological inhibition of histone deacetylase, therefore, is believed to induce the expression of represser genes in cancer tissue, inhibit the expression of tumor-promoting genes, and induce the expression of the redundant or back-up gene in patients suffering from various metabolic and hematological diseases. Thus, inhibition of histone deacetylase is proposed to slow the growth of neoplastic cells and/or reverse the deficient process of various metabolic and hematological diseases. Inhibition of histone deacetylase is also believed to play a role in antiprotozoal activity.

Trichostatin is the most potent inhibitor of histone deacetylase observed so far, but due to various drawbacks, such as availability of the material, has not been pursued.

Butyric acid is a natural product that has been known for several decades to be an effective differentiating and antiproliferative agent in a wide spectra of neoplastic cells in vitro. For example, butyric acid has been reported to induce cellular and biochemical changes in cancer cells, to induce apoptosis, and to increase the expression of transfected DNA, although the mechanism of action of butyric acid is unknown. Increased histone acetylation following treatment with butyric acid has been correlated with changes in transcriptional activity and at differentiated states of cells. Butyric acid and its salts, however, have shown low potency in both in vitro assays and clinical trials, and thus require large doses to achieve even minimal therapeutic effects. This can lead to fluid overload and mild alkalosis.

The present invention is directed to methods for using alkanoyloxymethyl ester compounds. The present compounds show significantly greater activity than butyric acid or its salts. That the present compounds have the ability to inhibit histone deacetylase has been previously unreported in the art.

SUMMARY OF THE INVENTION

The present invention relates to methods of treating a patient for an illness, particularly wherein the illness is one in which histone deacetylase inhibition would be beneficial. Examples include cancer, hemoglobinopathies and inherited metabolic disorders. Other illnesses and conditions that can be treated according to the present invention are discussed herein. In the case of histone deacetylase inhibition, the present compounds are believed to function by forming a coordinate bond with the zinc ion of histone deacetylase, thereby preventing its enzymatic activity; the inventor does not wish to be bound by this mechanism, however. The methods generally involve administering an effective amount of propionoyloxymethyl propionate, butyroyloxymethyl butyrate, or mixtures thereof to a patient.

It is therefore an aspect of the invention to provide methods for treating a patient using the present oxymethyl compounds.

A method for inhibiting histone deacetylase in a patient is also an aspect of the present invention.

These and other aspects of the invention will be apparent upon reviewing the attached specification and appended claims.

DETAILED DESCRIPTION OF THE INVENTION

Figure 1:
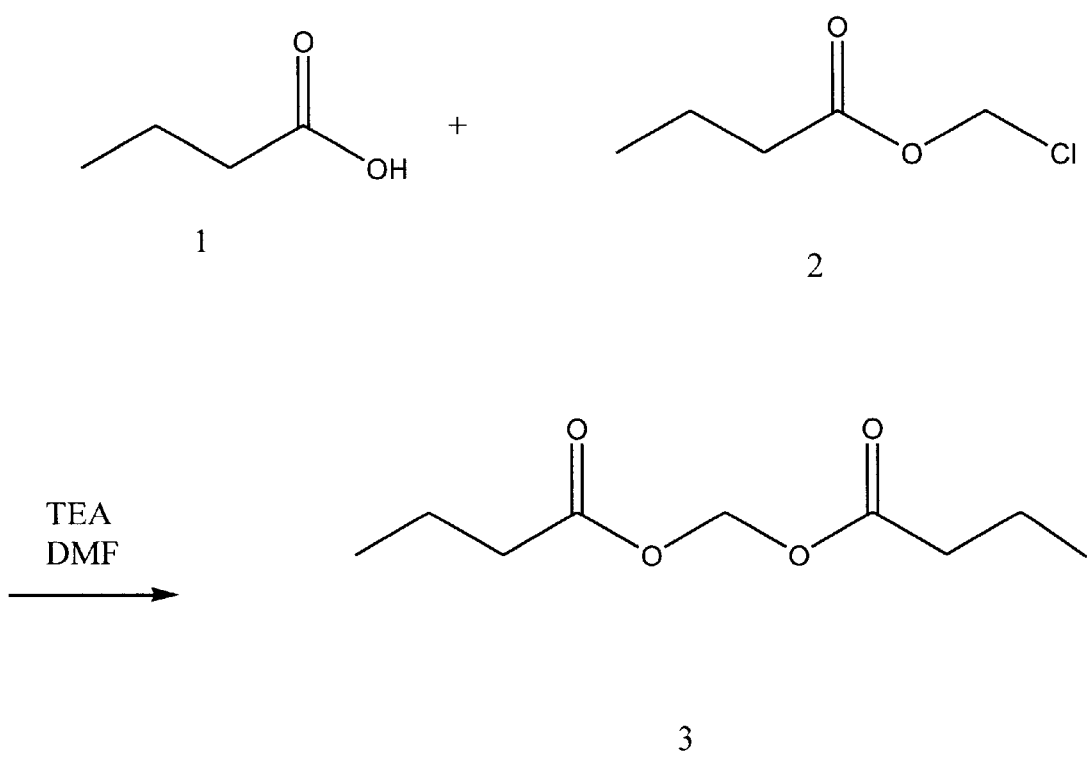
FIG. 1 shows a reaction scheme for preparing butyroyloxymethyl butyrate according to Example 1.

The present invention is directed to methods of using propionoyloxymethyl propionate ("POMP") and butyroyloxymethyl butyrate ("BOMB"), which will be understood by those skilled in the art as having the general formula (1):

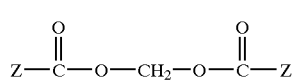

(1)

wherein Z is either —CH$_2$CH$_3$ (POMP) or —CH$_2$CH$_2$CH$_3$ (BOMB). More specifically, the present invention is directed to methods for treating an illness in a patient comprising administering to the patient an effective amount of POMP, BOMB, or combinations thereof.

Pharmaceutically acceptable salts of the above compounds are also within the scope of the invention. As used herein, "pharmaceutically acceptable salts" refer to derivatives of the disclosed compounds that are modified by making acid or base salts. Examples include, but are not limited to, mineral or organic acid salts of basic residues such as amines, alkali or organic base salts of acidic residues such as carboxylic acids, and the like. Pharmaceutically acceptable salts include, but are not limited to, hydrohalides, sulfates, methanesulfates, toluenesulfonates, nitrates, phosphates, maleates, acetates, lactates and the like.

Pharmaceutically-acceptable salts of the compounds of the present invention can be prepared by reacting the free acid or base forms of these compounds with a stoichiometric or greater amount of the appropriate base or acid in water or in an organic solvent, or in a mixture of the two; generally, nonaqueous media like ether, ethyl acetate, ethanol, isopropanol, or acetonitrile are preferred. The salts of the invention can also be prepared by ion exchange, for example. Lists of suitable salts are found in *Remington's Pharmaceutical Sciences*, 18$^{th}$ ed., Mack Publishing Company, Easton, Pa. (1990).

Generally, the present invention is directed to methods of treating illnesses in which proliferation of neoplastic or diseased cells occurs, or illnesses in which inhibition of histone deacetylase would be desired; as discussed above, inhibition of histone deacetylase results in the enhancement of gene expression that slows the growth of neoplastic cells and reverses the deficient process of various metabolic and hematological diseases. It will be understood that the present invention encompasses the treatment of various illnesses, as that term is defined herein, regardless of whether the treatment is through histone deacetylase inhibition, through another mechanism, or through a variety of mechanisms. The present compounds have a plasma half-life of sufficient length to effect a therapeutic benefit without requiring excessive doses, or doses that are toxic to a patient.

Illnesses treatable according to the present invention include, but are not limited to, various cancers, hematological diseases, and inherited metabolic diseases. Cancer includes, but is not limited to, leukemias, such as acute promyelocytic leukemia, acute myeloid leukemia, and acute myelomonocytic leukemia; other myelodysplastic syndromes; multiple myeloma such as breast carcinomas, cervical cancers, melanomas, colon cancers, nasopharyngeal carcinoma, non-Hodgkins lymphoma (NHL), Kaposi's sarcoma, ovarian cancers, pancreatic cancers, hepatocarcinomas, prostate cancers, squamous carcinomas, other dermatologic malignancies, teratocarcinomas, T-cell lymphomas, lung tumors, gliomas, neuroblastomas, peripheral neuroectodermal tumors, rhabdomyosarcomas, and prostate tumors and other solid tumors. Hematological diseases or hemoglobinopathies within the scope of the present invention include, but are not limited to, thalassemias, sickle cell anemias, infectious anemias, aplastic anemias, hypoplastic and hypoproliferative anemias, sideroblastic anemias, myelophthisic anemias, antibody-mediated anemias, anemias due to chronic diseases and enzyme-deficiencies, and anemias due to blood loss, radiation therapy and chemotherapy. Inherited metabolic diseases include, but are not limited to, Duschenne's muscular dystrophy, cystic fibrosis, and adrenoleukodystrophy. Thus, the term "illness" as used herein encompasses at least all of these things.

The term "illness" as used herein also encompasses various conditions such as cutaneous ulcers and gastrointestinal disorders. The cutaneous ulcers which can be treated in accordance with the current methods include leg and decubitus ulcers, stasis ulcers, diabetic ulcers and atherosclerotic ulcers. Gastrointestinal disorders treatable by the present methods include colitis, inflammatory bowel disease, Crohn's disease and ulcerative colitis. The term illness also refers to wounds such as abrasions, incisions, and burns.

"Illness" also encompasses treatment, prevention, or amelioration of virus-associated tumors including, but not limited to, EBV-associated malignancy, Kaposi's sarcoma, AIDS-related lymphoma, hepatitis B-associated malignancy or hepatitis C-associated malignancy. EBV-associated malignancy include, but are not limited to, nasopharyngeal carcinoma and non-Hodgkins' lymphoma. The present compounds can be administered in conjunction with a therapeutically effective amount of an antiviral agent such as ganciclovir, acyclovir and famciclovir. Protozoan infections are also included within "illness" and include, for example, malaria, cryptosporidiosis, trypanosomiasis, Eimeria sp., Plasmodiurn sp., toxoplasmosis, and coccidiosis.

In another embodiment of this invention, "illness" refers to alopecia, or hair loss. Alopecia is a common condition that results from diverse causes. In particular, alopecia frequently occurs in cancer patients who are treated with chemotherapeutic drugs and/or irradiation. Such agents damage hair follicles which contain mitotically active hair-producing cells. Such damage may cause abnormally slow growth of the hair or may lead to frank loss. Thus, the present invention further relates to methods for protecting against injury to hair follicles in a patient by administering one or more of the present compounds to the patient.

"Patient" refers to members of the animal kingdom, including but not limited to humans. Preferably, the methods of the present invention are applied to a patient suffering from any of the illnesses listed above.

The methods of the invention can be effected through administration of POMP and/or BOMB by any conventional means available for use in conjunction with pharmaceuticals, either as individual therapeutic agents or in combination with other therapeutic agents known in the art for the illness being treated. The compounds can be administered alone, but are generally administered with a pharmaceutically acceptable carrier selected on the basis of the chosen route of administration and standard pharmaceutical practice. The compositions of the invention may be adapted for oral, parenteral, topical, transdermal, transmucosal, rectal or intranasal administration, and may be in unit dosage form; the term "parenteral" as used herein includes subcutaneous, intravenous, intramuscular, or intrasternal injection or infusion techniques. Methods for preparing the present compositions for use by a patient are well known to those skilled in the pharmaceutical arts; formulations can include one or more fillers or preservatives in addition to the active ingredient and carrier.

"Pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Use of any of these media or agents is contemplated with the compounds of the present invention, absent compatibility problems with the active compound.

It is especially advantageous to formulate compositions in dosage unit form for ease of administration and uniformity of dosage. Dosage unit form as used herein refers to physically discrete units suited as unitary dosages for the patient to be treated, each unit containing a pre-determined quantity of active compound or "effective amount" calculated to produce the desired therapeutic effect in association with the pharmaceutical carrier. The specification for the dosage unit forms of the invention are dictated by and directly dependent on the characteristics of the active compound, the particular therapeutic effect to be achieved, and the limitations inherent in the art of compounding such an active compound for the treatment of sensitivity in individuals.

The appropriate dosage or "effective amount" administered in any given case will, of course, vary depending upon known factors, such as the pharmacodynamic characteristics of the particular compound and its mode and route of administration; the age, general health, metabolism, weight of the patient and other factors which influence response to the compound; the nature and extent of the illness being treated; the kind of concurrent treatment, if any; the frequency of treatment; and the effect desired. Generally, the effective amount will be that amount of the present compounds needed to inhibit histone deacetylase, without resulting in toxicity to the patient. Inhibition at any level is within the scope of the present invention and will contribute to a therapeutic benefit in a patient. A daily dosage of active ingredient will typically be between about 10 to 10,000 milligrams per meter$^2$ (mg/m$^2$) of body mass, with the preferred dose being 50–5,000 mg/m$^2$ body mass.

It will be appreciated that the therapeutic benefits of administration of the present compounds will be manifest in a variety of ways, depending on the patient and the illness being treated. More than one therapeutic benefit may be observed. The elicitation of any therapeutic benefit by the present methods is within the scope of the invention. "Treating" and "treatment" refer herein to both therapeutic and prophylactic treatments; for ease of reference, "therapeutic benefit" therefore refers collectively to both therapeutic and prophylactic benefits. Therapeutic benefits that may be achieved according to the present invention include, for example, retarding or eliminating tumor growth, apoptosis of tumor cells, healing wounds, healing cutaneous ulcers, ameliorating gastrointestinal disorders, modulating gene expression, inhibiting telomerase activity, inducing tolerance to antigens, preventing and/or ameliorating protozoan infection, inhibiting histone deacetylase in cells, modulating an immune response, ameliorating the effects of a cytotoxic agent, stimulating hematopoietic cells ex vivo and protecting hair follicles.

Modulation of an immune response can include, for example, enhancing cytokine secretion, inhibiting or delaying apoptosis in polymorphonuclear cells, enhancing polymorphonuclear cell function by augmenting hematopoietic growth factor secretion, inducing expression of cell surface antigens in tumor cells, and enhancing progenitor cell recovery after bone marrow transplantation.

Ameliorating the effects of a cytotoxic agent involves administering the present compounds in conjunction with the cytotoxic agent in such an amount so as to induce growth arrest of rapidly-proliferating epithelial cells of the patient, thereby protecting them from the cytotoxic effects of the agent. Cytotoxic agents, include, for example, chemotherapeutic agents, anticancer agents, and radiation therapy.

Modulating gene expression can be used to enhance, augment or repress the expression of a gene of interest. When expression of the gene of interest is to be enhanced or augmented, the gene can encode a gene product that is or acts as a repressor of another gene, a tumor suppressor, an inducer of apoptosis or an inducer of differentiation. Enhancing recombinant gene expression can be effected in a number of cells; the gene product can be any protein or peptide of interest such as tumor suppression genes. When expression of the gene of interest is to be repressed, the gene can encode a gene product that is or acts as an oncogene or an inhibitor of apoptosis, such as the bcl2 gene.

Inhibition of telomerase activity in cancer cells inhibits the malignant progression of the cells.

Inducing tolerance to an antigen is preferably carried about with a self-antigen, such as those associated with an autoimmune disease such as systemic lupus erythromatosus, rheumatoid arthritis, multiple sclerosis or diabetes. Tolerance can also be induced to one or more antigens present on a transplanted organ or cells.

The present invention is also directed a pharmaceutical composition comprising the compounds of formula 1 within a pharmaceutically acceptable carrier.

EXAMPLES

The following examples are intended to illustrate the invention, and should not be construed as limiting the invention in any way.

Example 1

Preparation of Butyroyloxymethyl Butyrate 3

Reference numerals correspond with those of FIG. 1.

A solution of 137.6 g of butyric acid 1 and 193.8 g of chloromethyl butyrate 2 in 550 mL of anhydous DMF in a 4-necked 2-L round bottom flask was cooled to about 12° C. and the cooling bath was removed. To this solution was added dropwise 250 mL of TEA under a nitrogen atmosphere over about 1.2 hours. The temperature of the reaction mixture reached 23° C. upon completion of addition. The resulting reaction mixture was stirred at ambient temperature for 20 hours.

An aliquot was then removed from the reaction mixture. Water and ethyl acetate were added. The ethyl acetate layer was removed, washed with water, and dried. GC of the ethyl acetate layer showed unreacted chloromethyl butyrate (based on the GC retention time, 3.44 min. 16.8%) and the product 3 (6.11 min, 83.2%). An additional 12 mL of butyric acid and 20 mL of TEA were added and the resulting mixture was heated at between 30 and 33° C. for about one hour. After that, the heating source was removed and stirred at ambient temperature for six hours. The reaction mixture was filtered and the cake was thoroughly washed with about 700 mL of ethyl acetate. The combined filtrates were poured into 500 g of ice, 500 mL of water and 1 L of ethyl acetate. The organic layer was separated, washed sequentially is with 1 L of water, 750 mL of saturated NaHCO$_3$ (2×), brine (750 mL), dried over MgSO$_4$, and concentrated in vacuo to give the crude product as a colored oil.

The crude product 3 from the reaction of butyric acid 1 and chloromethyl butyrate 2 was Kugelrohred at 60° C./0.1 mm to give the product 3 as a colorless oil. The high boiler colored-impurities remained in the flask. $^1$H NMR(CDCl$_3$) of the oil sowed the presence of trace amount of ethyl acetate. This was concentrated on a rotavap to remove the trace amount of ethyl acetate; 232 g of the desired product as a colorless oil resulted. $^1$H NMR(CDCl$_3$) δ 5.76 (s, 2H), 2.35 (t, 4H), 1.67 (m, 4H), 0.96 (t, 6H); $^{13}$C NMR(CDCl$_3$), 172.93, 80.07, 36.71, 19.03, 14.29 (86.3% yield).

A summary of components used is provided in Table 1.

TABLE 1

| compound | MW | mol used | wt. used | eq | density | vol used |
|---|---|---|---|---|---|---|
| butyric acid 1 | 88.11 | 1.56 | 137.6 | 1.1 | — | — |
| chloromethyl butyrate 2 | 136.6 | 1.42 | 193.8 g | 1 | — | — |
| DMF | — | — | — | — | — | 550 mL |
| TEA | 101 | 1.8 | 181 | 1.26 | 0.726 | 250 mL |

Example 2

Preparation of Propionoyloxymethyl Propionate 8

Figure 2A:
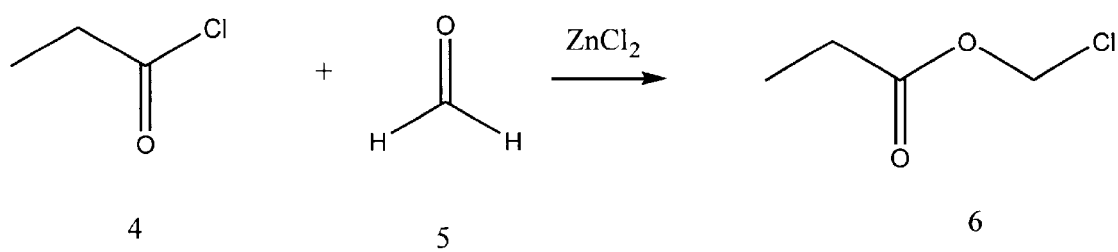
FIG. 2 shows a reaction scheme for preparing propionoyloxymethyl propionate according to Example 2.
Figure 2B:
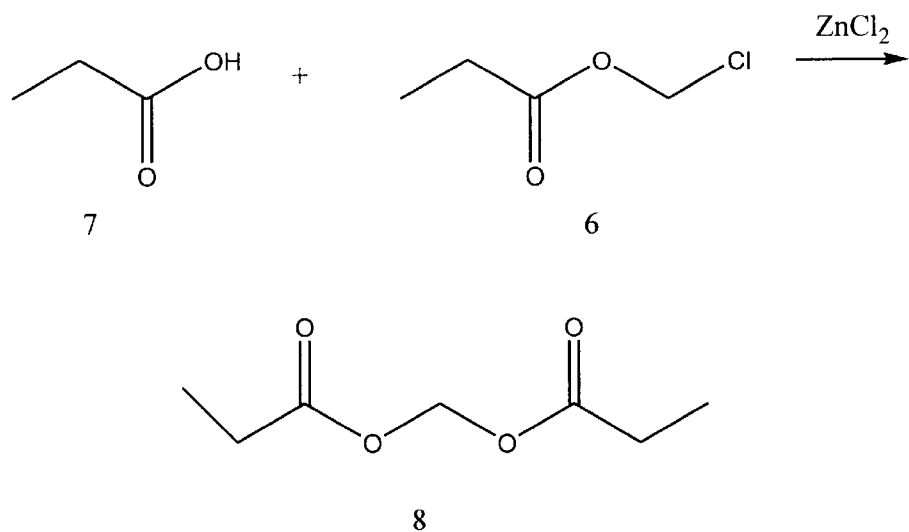

Reference numerals correspond with those of FIG. 2.

Zinc chloride (4.1 g) was added portionwise to a solution of 1945.5 mL of propionyl chloride 4 and 672 g of paraformaldehyde 5 and the resulting solution was heated to reflux and monitored by NMR. The reaction was violently exothermic, heated up to 105° C. and refluxed out the top of the reflux condenser before ½ of the zinc chloride had been added. The reaction mixture cooled back to about 78° C. and the rest of the zinc chloride was added. The mixture was heated at 78° C. overnight. The reaction mixture was distilled at atmospheric pressure with a 20 cm Vigreaux column to separate chloromethyl propionate 6 from impurities.

Chloromethyl propionate 6 was then reacted with propionic acid 7 in the manner described in Example 1 for chloromethyl butyrate and butyric acid. The product 8 was the result.

A summary of the components used is provided in Table 2.

TABLE 2

| Compound | MW | moles | grams | mL | Density |
|---|---|---|---|---|---|
| $ZnCl_2$ | 136.28 | 0.03 | 4.1 | — | — |
| propionyl chloride 4 | 92.52 | 22.40 | 2072.0 | 1945.5 | 1.065 |
| formaldehyde 5 | 30 | 22.40 | 672.0 | — | — |

Example 3

The compounds prepared according to Examples 1 and 2 were tested for anti-proliferation against PC-3 prostate cancer cells. Trichostatin, a potent HDAC inhibitor, was purchased from Sigma-Aldrich, Milwaukee, Wis. and was used as a reference compound.

The PC-3 cell line was maintained in RPMI supplemented with 10% fetal calf serum and antibiotics. The EDR assay was performed as described by Kern and Weisenthal in "Highly Specific Prediction of Antineoplastic Drug Resistance With An In Vitro Assay Using Suprapharmacologic Drug Exposures," *J Nat. Cancer Inst.*, 82:582–588 (1990); and Fruehauf and Bosanquet, "In vitro Determination of Drug Response: A Discussion of Clinical Applications," PPO Updates 7(12):1–16 (1993). Cells were suspended in 0.12% soft agar in complete medium and plated (2,000 cells per well, as determined by preliminary experiments) in different drug concentrations onto a 0.4% agarose underlayer in 24-well plates. Plating cells on agarose underlayers supports the proliferation only of the transformed cells, ensuring that the growth signal stems from the malignant component of the tumor.

All compounds were dissolved in DMSO to 200× stock solutions. Stock solutions were diluted to 20× working solutions using the tissue culture medium, serially diluted and added to the 24-well plates. The concentration range was 0.001 $\mu$M to 0.3 $\mu$M for trichostatin and 10 $\mu$M–1,000 $\mu$M for the other compounds. No significant changes in pH of the culture medium were observed under the above conditions. Diluent control wells contained PC3 cells treated with DMSO, at the dilutions used for appropriate drug treatment. All experimental points were represented by two separate wells (duplicates). Positive controls were determined using at least two wells treated with an extremely high dose of cisplatin, an anti-cancer agent. Four wells containing tumor cells that were not treated with drugs served as negative controls in each experiment.

Cells were incubated with drugs under standard culture conditions for five days. Cultures were pulsed with tritiated thymidine ($^3$H-TdR, New Life Science Products, Boston, Mass.) at 5 $\mu$Ci per well for the last 48 hours of the culture period. Cell culture plates were then heated to 90° C. to liquefy the agarose, and cells were harvested onto glass fiber filters, which were then placed into counting vials containing liquid scintillation fluid. The radioactivity trapped on the filters was counted with a Beckman scintillation counter. The fraction of surviving cells was determined by comparing $^3$H-TdR incorporation in treated (experimental points) and untreated (negative control) wells. All drug concentrations are presented as $\mu$M, allowing for normalization of drug response curves and direct comparison of the effects of the drugs. Microsoft Excel was used to organize the raw data on EDR experiments, and the SigmaPlot program was utilized to generate drug response curves. All drug response curves were as approximated as sigmoidal equations (characteristic for typical drug response curves) to fit the data. $IC_{50}$ values were determined using the approximated sigmoidal curves and expressed as $\mu$M.

Table 3 provides the PC-3 $IC_{50}$ data for each of the compounds tested.

TABLE 3

| COMPOUND | PC-3 $IC_{50}$ ($\mu$M) |
|---|---|
| propionoyloxymethyl propionate | 30 |
| butyroyloxymethyl butyrate | 40 |
| butyric acid | >2,000 |
| trichostatin | 0.005 |

As can be seen from Table 3 both POMP and BOMB are much more active than butyric acid in the cancer cell.

Example 4

POMP and BOMB were tested for histone deacetylase inhibition. Trichostatin and butyric acid, which are known inhibitors of histone deacetylase, were used for comparative examples.

The inhibition of histone deacetylase was determined according to methods generally described by Hoffmann et al., *Nucleic Acids Res.* 27:2057–8 (1999). The histone deacetylase was isolated from rat liver as previously described by M. Tung. The compounds tested were initially dissolved in either ethanol or in DMSO to provide working stock solutions.

The assay was performed in a final volume of 120 $\mu$L total, consisting of 100 $\mu$L of 15 $\mu$M tris-HCl buffer (pH 7.9) also containing 0.25 $\mu$M EDTA, 10 $\mu$M NaCl, 10% glycerol, 10 $\mu$M mercaptoethanol and the enzyme. The assay was initiated upon the addition of 10 ml of one of the compounds being tested, followed by the addition of the fluorescence-labeled lysine substrate to each assay tube in an ice bath for 15 minutes. The tubes were transferred to a water bath at 37° C. for an additional 90 minutes.

The fluorescent substrate described by Hoffmann was modified to increase the precision and accuracy by the addition of an internal standard for the HPLC determination. The synthetic substrate, MAL is N-(4-methyl-7-coumarinyl)-N-α(tert-butyloxy-carbonyl)-N-Ω-acetyllysineamide.

An initial assay was performed to determine the range of activity of each compound. The determination of $IC_{50}$-values was made from the results of five dilutions in range according to the expected potency for each compound. All values are the result of two or more experiments.

Since it was considered that some of these compounds may be metabolized by esterases in the enzyme preparation, certain compounds were tested in the presence of the esterase inhibitor, PMSF. There was no effect of PMSF upon the inhibition of the enzyme by those compounds tested.

TABLE 4

| COMPOUND | HDAC($\mu$M) |
|---|---|
| Trichostatin | 0.03 |
| Butyric acid | 4,500 |
| POMP | 590 |
| BOMB | 1,420 |

As can be seen from Table 4, both POMP and BOMB are more active than butyric acid as inhibitors of histone deacetylase.

Whereas particular embodiments of this invention have been described above for purposes of illustration, it will be evident to those skilled in the art that numerous variations of the details of the present invention may be made without departing from the invention as defined in the appended claims.

What is claimed is:

1. A method for inhibiting histone deacetylase in cells comprising administering to said patient an effective amount of a composition consisting essentially of propionoyloxymethyl propionate or butyroyloxymethyl butyrate, whereby said method results in the treatment of cancer in a patient.

2. The method of claim 1, wherein said composition is contained in a pharmaceutically acceptable carrier.

3. The method of claim 1, wherein said effective amount is at least about 10 milligrams per meter$^2$ of body mass, per day.

4. The method of claim 1, wherein said composition is administered orally, parenterally, transdermally, transmucosally, intranasally, rectally or topically.

5. The method of claim 1, wherein said effective amount is an amount sufficient to effect a therapeutic benefit.

6. The method of claim 1, wherein said composition consists essentially of propionoyloxymethyl propionate.

7. The method of claim 1, wherein said composition consists essentially of butyroyloxymethyl butyrate.

8. A method for inhibiting histone deacetylase comprising administering an effective amount of a composition consisting essentially of propionoyloxymethyl propionate or butyroyloxymethyl butyrate to a sample including histone deacetylase.

9. The method of claim 8, wherein propionoyloxymethyl propionate is administered.

10. The method of claim 8, wherein butyroyloxymethyl butyrate is administered.

11. The method of claim 8, wherein the sample includes a cell containing said histone deacetylase.

12. A method for inhibiting histone deacetylase in a patient comprising administering to the patient an effective amount of a composition consisting essentially of propionoyloxymethyl propionate, whereby said method results in retarding prostatic tumor growth.

13. The method of claim 12, wherein said composition is contained in a pharmaceutically acceptable carrier.

14. The method of claim 12, wherein said composition is administered orally, parenterally, transdermally, transmucosally, intranasally, rectally or topically.

15. The method of claim 12, wherein said effective amount is an amount sufficient to effect a therapeutic benefit.

16. A method for retarding prostatic tumor growth in a patient comprising administering to said patient an effective amount of a composition consisting essentially of propionoyloxymethyl propionate or butyroyloxymethyl butyrate.

17. The method of claim 16, wherein said composition consists essentially propionoyloxymethyl propionate.

18. The method of claim 16, wherein said composition consists essentially of butyroyloxymethyl butyrate.

19. A method for treating the proliferation of prostate cancer cells in a patient comprising administering to said patient an effective amount of a composition consisting essentially of propionoyloxymethyl propionate or butyroyloxymethyl butyrate.

20. The method of claim 19, wherein said composition consists essentially of propionoyloxymethyl propionate.

21. The method of claim 19, wherein said composition consists essentially of butyroyloxymethyl butyrate.

* * * * *